United States Patent
Trinkel

(10) Patent No.: US 6,792,324 B2
(45) Date of Patent: Sep. 14, 2004

(54) DEVICE FOR DETERMINING AND CHARACTERIZING NOISES GENERATED BY MASTICATION OF FOOD

(76) Inventor: Marian Trinkel, Waschpöl 14 b, D-53272 Kreuzau (DE)

(*) Notice: Subject to any disclaimer, the term of this patent is extended or adjusted under 35 U.S.C. 154(b) by 730 days.

(21) Appl. No.: 09/736,590

(22) Filed: Dec. 13, 2000

(65) Prior Publication Data

US 2001/0025202 A1 Sep. 27, 2001

(30) Foreign Application Priority Data

Dec. 13, 1999 (DE) .......................................... 199 60 014

(51) Int. Cl.⁷ .......................... G06F 17/00; H04R 29/00; H03B 29/00
(52) U.S. Cl. .......................... 700/94; 381/56; 381/151; 381/71.7
(58) Field of Search .......................... 700/94; 381/71.7, 381/56, 71.1, 151; 181/128; 73/821

(56) References Cited

U.S. PATENT DOCUMENTS 5,067,488 A * 11/1991 Fukada et al. .............. 600/590
5,692,059 A * 11/1997 Kruger ...................... 381/151
5,827,974 A * 10/1998 Nussinovitch et al. ........ 73/821
5,933,506 A * 8/1999 Aoki et al. .................. 381/151

FOREIGN PATENT DOCUMENTS

| DE | 23 13 833 | 10/1974 |
|---|---|---|
| DE | 35 09 376 | 11/1985 |
| DE | 37 36 515 | 5/1989 |
| DE | 42 16 924 | 11/1993 |
| WO | WO 81/03702 | 10/1981 |

OTHER PUBLICATIONS

Management Circle, "Akustik–Design in der Lebensmittelindustrie" Jan. 1999.
Krrrrrrrrk, "Welt der Wissenschaft" 1999.

* cited by examiner

Primary Examiner—Stella Woo
(74) Attorney, Agent, or Firm—Gudrun E. Huckett

(57) ABSTRACT

A device for determining and characterizing noises generated by masticating food has an enclosure and a mastication device arranged in the enclosure. One or more first reception microphones for airborne sound are arranged in the enclosure. The enclosure is advantageously a dummy head for audio recording. Preferably, two such first reception microphones are arranged in the enclosure. Two second reception microphones for sound conducted by solid material, simulating bone conduction, may be provided in order to create a sound as near-natural as possible.

15 Claims, 4 Drawing Sheets

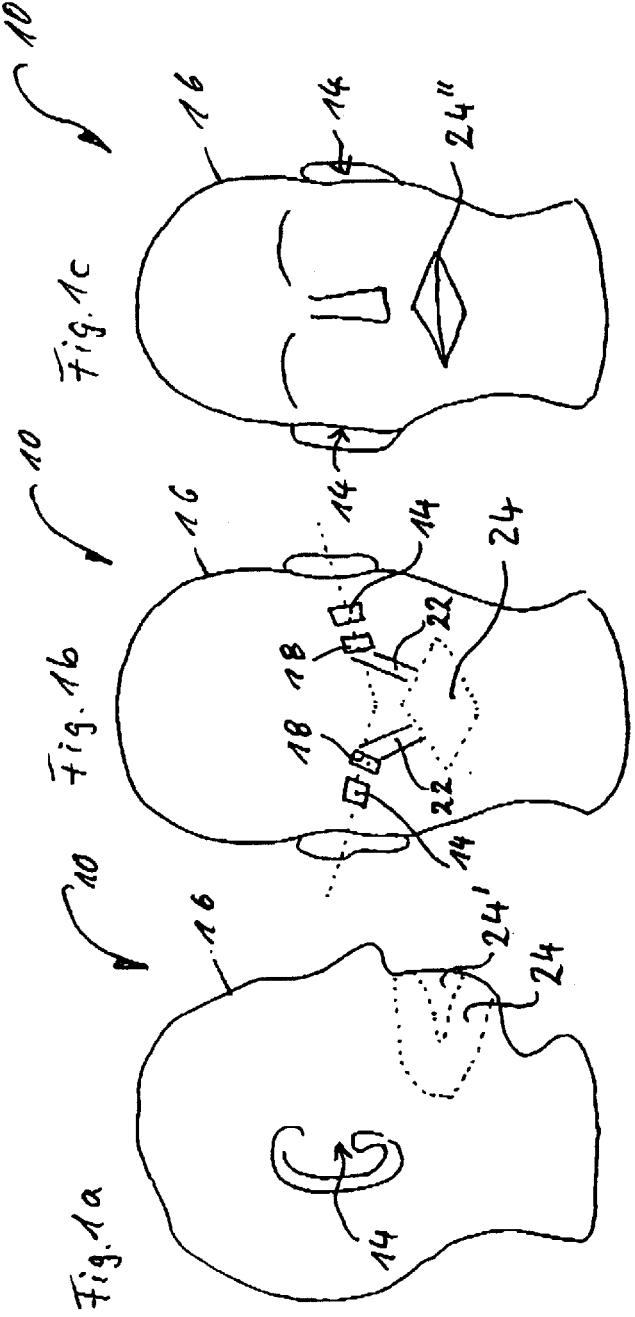

DEVICE FOR DETERMINING AND CHARACTERIZING NOISES GENERATED BY MASTICATION OF FOOD

BACKGROUND OF THE INVENTION

1. Field of the Invention

The invention relates to a device for determining and characterizing noises generated by mastication of food, wherein the device comprises a mastication device and at least one reception microphone.

2. Description of the Related Art

A device of the aforementioned kind is known. Recently, the food industry has found it to be advantageous to consider the chewing or mastication noises generated by food in order to improve sales, and, consequently, the Nestlé Research Center, for example, has developed a so-called acusto-mechanical device for determining and characterizing the so-called crispness, i.e., the noise developed during mastication of food.

In this context, crispness is considered a quality feature for texture, wherein the texture is the entirety of impressions which are sensed when food is touched, cut, spread, pricked, poured, bitten into, or chewed and swallowed.

It is known that food often has a heterogeneous structure, i.e., a macro structure as, for example, bread crumbs or the crust of bread.

The texture, however, indicates a structure that is "invisible" because these structural units are microscopically small.

The sensations which occur during a texture determination can be differentiated as follows: soft, solid, hard, crumbly, crisp, brittle, smooth, rubber-like tacky, pasty, slippery; as well as clear, viscous, slimy; and also sandy, grainy, coarse, fibrous and crystalline.

The so-called crispness is an important sensory quality feature of the texture of the product.

This crispness is often a desired feature of various foods, for example, breakfast cereals, sweets, baked goods, vegetables, fruits, and others.

The Nestlé company was able to determine crispness with the aid of the aforementioned acusto-mechanical device.

In this connection, the food to be examined was crushed or masticated by means of a masticator, and the noise resulting therefrom was recorded by means of a microphone.

However, in this connection only the so-called airborne sound was recorded, but not the noises which are conducted during chewing via the bones into the inner ear, the so-called bone-conducted sound.

This has the consequence that this device cannot determine or characterize a complete impression of the noises occurring during chewing.

Further methods for determining and characterizing the mastication noises reside in that test persons chew the foods to be tested and evaluate the noises that are caused by the chewing action.

This is not only very time-consuming because each test person requires approximately six minutes to complete each test run, but of much greater consequence is the fact that all test persons report different, i.e., substantially subjective, sensations, so that the test results are not at all reproducible.

SUMMARY OF THE INVENTION

It is an object of the present invention to provide a method of the aforementioned kind which makes possible a simple, near-natural, inexpensive determination and characterization of mastication noises of foods.

In accordance with the present invention, this is achieved for a device of the aforementioned kind by an enclosure in which the mastication device as well as the at least one reception microphone are arranged.

This makes a near-natural determination of the mastication noises possible.

In order to improve the simulation of human sensation even further, it is advantageous when a further reception microphone is provided.

According to an especially advantageous embodiment of the invention, the enclosure is a Kunstkopf (dummy head) for audio recording.

In order for the bone-conducted sound to be simulated as identically as possible, it is advantageous when two additional (second) reception microphones are used which are designed such that they receive sound introduced into solid materials, while the two other (first) reception microphones are designed to receive the airborne sound.

Since after comminuting the food it is mainly the tongue that is active during the chewing process, it is advantageous to provide a chewing device for simulating the tongue action during the chewing process.

This chewing device can be a membrane which is actuated electrically, mechanically, pneumatically or is loaded (actuated) by a liquid.

According to a further embodiment of the invention, it is proposed to correlate or pair each additional (second) reception microphone with one of the two other (first) reception microphones, respectively, and to acoustically decouple the correlated (paired) reception microphones.

Moreover, it is possible to connect each of the additional (second) reception microphones by means of an acoustic bridge with a testing chamber in which the mastication device is arranged in order to simulate the bone conduction of sound even better.

Since during a chewing process salivation also plays a role in affecting the acoustics, it is advantageous to provide a moistening device for moistening the food.

Moreover, it is possible to ensure the acoustic conditions to be even more near-natural by providing a heating device for appropriately heating the food.

When a closeable opening is present, the simulation of the chewing process for an open as well as a closed mouth is possible.

According to a further embodiment of the invention, a control device is provided for controlling the determination and characterization process. This control device can be actuated manually or can perform the control function automatically.

For processing the acoustic measuring results, a processing unit can also be provided.

BRIEF DESCRIPTION OF THE DRAWING

In the drawing:

FIG. 1a is a side view of a dummy head illustrating in dashed lines the outline of the testing chamber;

FIG. 1b is a front view of the dummy head, showing portions of the interior to illustrate the reception microphone positions in the dummy head;

FIG. 1c is a front view of the dummy head;

FIG. 1d is a detail view of the arrangement of the first and second reception microphones;

DESCRIPTION OF THE PREFERRED EMBODIMENTS

Figure 2A:
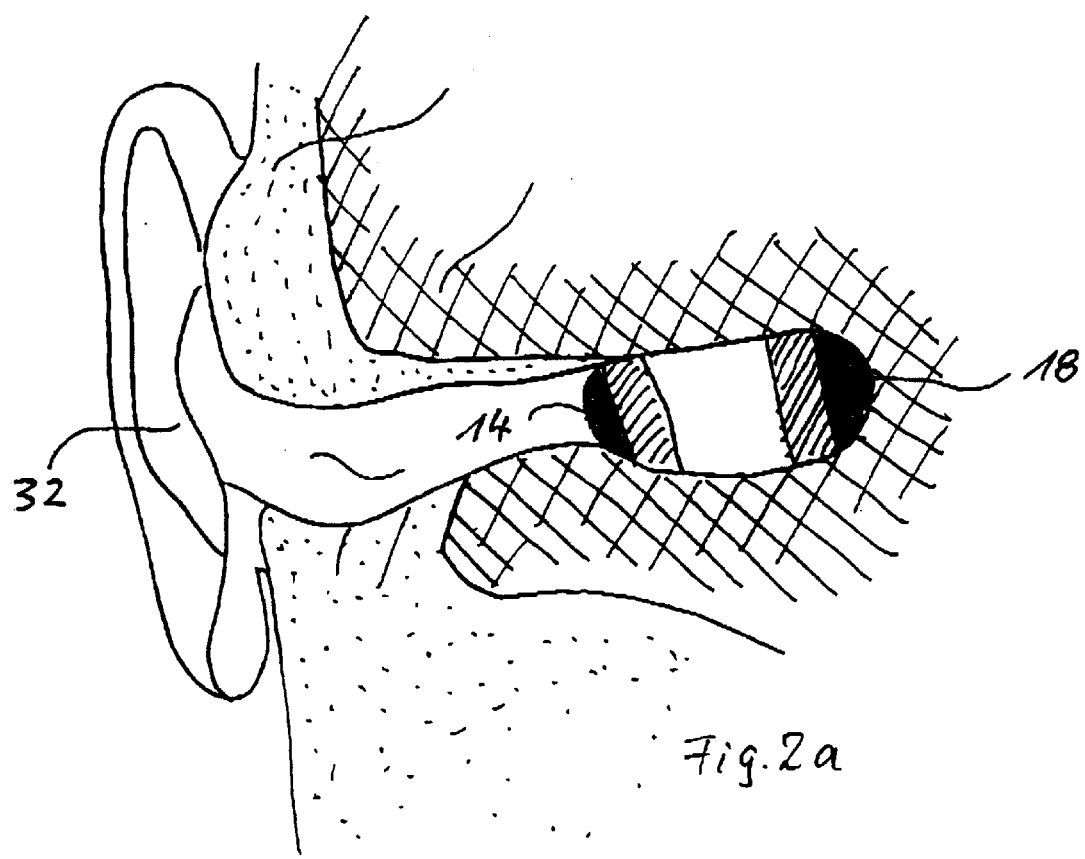
FIG. 2a is a sectional view for illustrating the arrangement of the reception microphones in the dummy head.

With the aid of FIGS. 1a–1d, 2a–2b, 3, and 4 several embodiments of a device 10 for determining and characterizing noises generated by mastication of food will be explained.

This device 10 comprises a mastication device 12 and at least one reception microphone 14 which are both arranged in an enclosure 16.

In the illustrated embodiments the enclosure is a Kunstkopf (dummy head) 16 for audio recording; see, in particular, FIGS. 1a–1c.

In accordance with the dummy head design, two (first) reception microphones 14 as well as two correlated additional (second) reception microphones 18 are arranged in the auditory canals; see FIG. 1b.

Figure 2B:
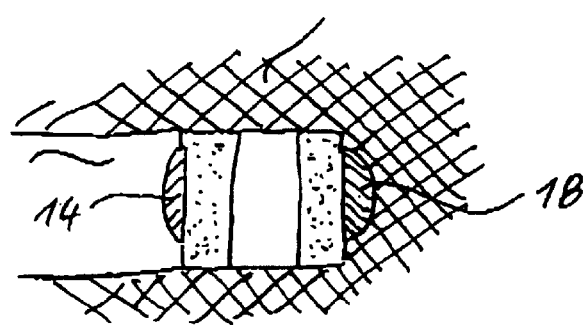
FIG. 2b shows a detail view of the arrangement of the reception microphones.

In this context, the two first reception microphones 14 are provided for receiving airborne sound, while the additional (second) reception microphones 18 rests against solid material and thus receive sound conducted through the solid material (see FIGS. 2a, 2b).

As can be seen in FIG. 2a, the airborne sound enters via the sound inlet 32 into the auditory canal and impinges on the reception microphone 14.

Figure 3:
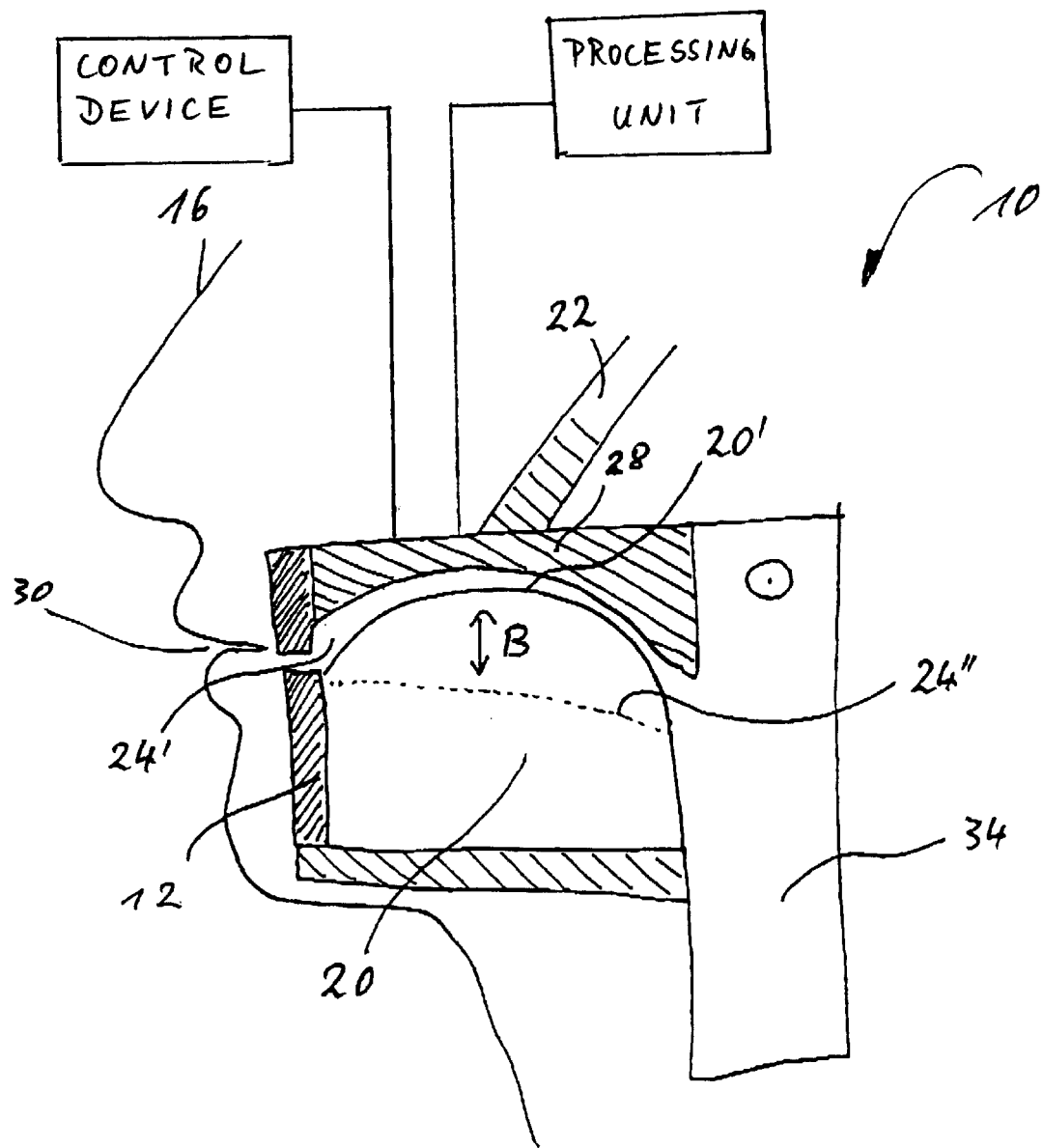
FIG. 3 is a partial section view of an embodiment of the present invention.

As can be seen, in particular, in FIG. 3, the mastication device 12 comprises a chewing device 20 which simulates the chewing action performed by a tongue.

This chewing device 20 comprises a membrane 20' which can be moved electrically, mechanically, pneumatically, or by being loaded (actuated) by a liquid in the direction of double arrows B.

In the area of the palate, the embodiment according to FIG. 3 has a heating device 28 which serves for heating the food to be masticated appropriately.

In order for the so-called bone-conducted sound to be transmitted as near-naturally as possible, the device 10 is provided with an acoustic bridge 22, as illustrated in FIG. 3 (see also FIGS. 1b and 1d), which connects the mastication device 12, i.e., the testing chamber 24 of the mastication device 12, with the additional reception microphones 18.

In FIG. 3, the testing chamber 24 is illustrated in a tight state identified by 24', i.e., the mouth is in a substantially closed position, while the dash-dotted line identified by 24" shows the open state, i.e., the essentially open mouth.

The different states of open or closed mouth can also be simulated by means of an opening 30 which can be opened or closed as needed.

In the rearward portion of the dummy head 16, essentially opposite the mouth (opening 30), a sample collecting container 34 is provided which receives the tested food.

Figure 4:
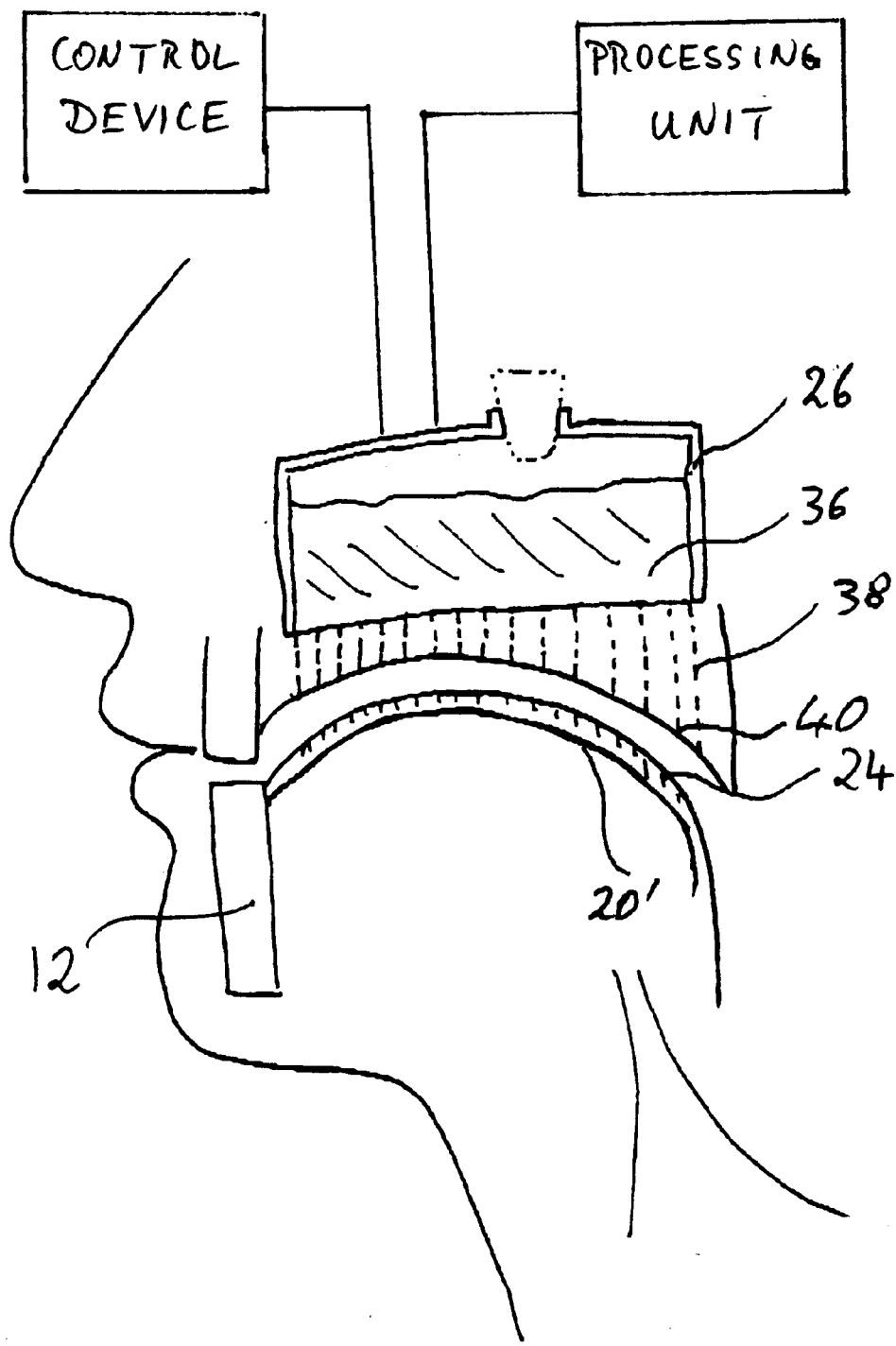
FIG. 4 is a partial section view of another embodiment of the present invention.

FIG. 4 shows a further embodiment of the device 10 for determining and characterizing noises generated by mastication of food.

The embodiment according to FIG. 4 comprises a moisturizing device 26 with which liquid 36 can be supplied through capillaries 38 and openings 40 into the mastication device 12, i.e., the testing chamber 24.

Of course, the features of the embodiments according to FIG. 3 and according to FIG. 4, respectively, can also be combined with one another.

A control device, illustrated only schematically in the Figures since it is generally well known in the art, controls the determination and characterization process of the noises generated by mastication of the food. In this context, it is possible to actuate the control device either manually or to provide an automatically operating control device. This can be realized, for example, by suitable programs which are stored in the control device.

A processing unit, also only schematically illustrated in the Figures since it is generally well known in the art, carries out the processing of the acoustic test results.

By means of the above embodiments of the invention, it is possible to determine noises, generated by mastication of food, in a near-natural, simple, inexpensive, and quick way.

While specific embodiments of the invention have been shown and described in detail to illustrate the inventive principles, it will be understood that the invention may be embodied otherwise without departing from such principles.

What is claimed is:

1. A device (10) for determining and characterizing noises generated by masticating food, said device (10) comprising:
   an enclosure (16);
   a mastication device (12) arranged in said enclosure (16); and
   one or more first reception microphones (14) arranged in said enclosure (16);
   wherein said mastication device (12) comprises a chewing device (20) configured to stimulate a chewing action performed by a tongue.

2. The device (10) according to claim 1, wherein two of said first reception microphones (14) are arranged in said enclosure (16).

3. The device (10) according to claim 2, further comprising two second reception microphones (18) configured to receive sound conducted in solid materials, wherein said two first reception microphones (14) are configured to receive airborne sound.

4. The device (10) according to claim 3, wherein each one of said second reception microphones (18) is correlated with one of said first reception microphones (14) to form a microphone pair (14, 18) and wherein each one of said microphone pairs (14, 18) is acoustically decoupled.

5. The device (10) according to claim 3, wherein said mastication device (12) comprises a testing chamber (24).

6. The device (10) according to claim 1, wherein said chewing device (20) comprises a membrane (20') configured to be actuated electrically, mechanically, pneumatically, or by liquid loading.

7. The device (10) according to claim 1, further comprising a moisturizing device (26) for moisturizing the food.

8. The device (10) according to claim 1, further comprising a heating device (28) for heating the food to an appropriate temperature.

9. A device (10) for determining and characterizing noises generated by masticating food, said device (10) comprising:
   an enclosure (16);
   a mastication device (12) arranged in said enclosure (16); and
   one or more first reception microphones (14) arranged in said enclosure (16);

wherein said enclosure (16) has a closeable opening (30) for simulating a chewing process with open mouth and closed mouth.

10. The device (10) according to claim 1, further comprising a control device for controlling a determination and characterization process of said device (10).

11. The device (10) according to claim 10, wherein said control device is configured to be manually actuated.

12. The device (10) according to claim 10, wherein said control device is configured to operate automatically.

13. The device (10) according to claim 1, further comprising a processing unit configured to process acoustic measuring results obtained during a determination and characterization process.

14. A device (10) for determining and characterizing noises generated by masticating food, said device (10) comprising:
- an enclosure (16);
- a mastication device (12) arranged in said enclosure (16); and
- one or more first reception microphones (14) arranged in said enclosure (16);
- wherein said enclosure (16) is a dummy head for audio recording.

15. A device (10) for determining and characterizing noises generated by masticating food, said device (10) comprising:
- an enclosure (16);
- a mastication device (12) arranged in said enclosure (16), wherein said mastication device (12) comprises a testing chamber (24);
- two first reception microphones (14) arranged in said enclosure (16);
- two second reception microphones (18) configured to receive sound conducted in solid materials, wherein said two first reception microphones (14) are configured to receive airborne sound;
- wherein said mastication device (12) comprises a testing chamber (24);
- a first acoustic bridge (22) and a second acoustic bridge (22), wherein said first acoustic bridge (22) connects a first one of said second reception microphones (18) to said testing chamber (24) and said second acoustic bridge (22) connects a second one of said second reception microphones (18) to said testing chamber (24).

* * * * *